(12) United States Patent
Blum-Sperisen et al.

(10) Patent No.: US 10,137,108 B2
(45) Date of Patent: Nov. 27, 2018

(54) NUTRITIONAL COMPOSITION USEFUL IN THE TREATMENT OF IBD PATIENTS

(71) Applicant: NESTEC S.A., Vevey (CH)

(72) Inventors: Stephanie Blum-Sperisen, Pully (CH); Magali Faure, Forel (CH); Denis Breuille, Lausanne (CH); Emil Chuang, Vevey (CH)

(73) Assignee: Nestec S.A., Vevey (CH)

( * ) Notice: Subject to any disclaimer, the term of this patent is extended or adjusted under 35 U.S.C. 154(b) by 0 days.

(21) Appl. No.: 15/544,088

(22) PCT Filed: Jan. 22, 2016

(86) PCT No.: PCT/EP2016/051275
§ 371 (c)(1),
(2) Date: Jul. 17, 2017

(87) PCT Pub. No.: WO2016/116580
PCT Pub. Date: Jul. 28, 2016

(65) Prior Publication Data
US 2017/0368027 A1    Dec. 28, 2017

(30) Foreign Application Priority Data
Jan. 23, 2015  (EP) ..................................... 15152309

(51) Int. Cl.
| | | |
|---|---|---|
| *A01N 47/00* | (2006.01) |
| *A61K 31/21* | (2006.01) |
| *A61K 31/26* | (2006.01) |
| *A61K 31/401* | (2006.01) |
| *A23L 2/00* | (2006.01) |
| *A61K 31/198* | (2006.01) |
| *A61K 31/20* | (2006.01) |
| *A61K 31/202* | (2006.01) |
| *A61K 31/70* | (2006.01) |
| *A61K 31/715* | (2006.01) |
| *A61K 31/718* | (2006.01) |
| *A61K 35/20* | (2006.01) |
| *A61K 38/18* | (2006.01) |
| *A61K 31/201* | (2006.01) |

(52) U.S. Cl.
CPC .............. *A61K 31/401* (2013.01); *A23L 2/00* (2013.01); *A61K 31/198* (2013.01); *A61K 31/20* (2013.01); *A61K 31/201* (2013.01); *A61K 31/202* (2013.01); *A61K 31/70* (2013.01); *A61K 31/715* (2013.01); *A61K 31/718* (2013.01); *A61K 35/20* (2013.01); *A61K 38/1841* (2013.01); *A23V 2250/064* (2013.01); *A23V 2250/0642* (2013.01); *A23V 2250/0648* (2013.01); *A23V 2250/1868* (2013.01); *A23V 2250/28* (2013.01); *A23V 2250/50* (2013.01); *A23V 2250/54252* (2013.01)

(58) Field of Classification Search
None
See application file for complete search history.

(56) References Cited

U.S. PATENT DOCUMENTS

| | | | |
|---|---|---|---|
| 5,719,134 A | 2/1998 | Schmidl et al. | |
| 5,952,314 A | 9/1999 | DeMichele et al. | |
| 8,075,934 B2 * | 12/2011 | Banavara ........... | A61K 38/1841 426/72 |
| 2004/0097714 A1 | 5/2004 | Maubois et al. | |
| 2009/0238893 A1 * | 9/2009 | Langford ................ | A23L 33/40 424/602 |
| 2011/0257110 A1 * | 10/2011 | Kharazmi .......... | A61K 31/7032 514/25 |

FOREIGN PATENT DOCUMENTS

| | | |
|---|---|---|
| EP | 0689835 | 1/1996 |
| EP | 1920770 | 5/2008 |
| WO | 2008001086 | 1/2008 |

OTHER PUBLICATIONS

Faure et al., "Specific Amino Acids Increase Mucin Synthesis and Microbiota in Dextran Sulfate Sodium-Treated Rats," J. Nutr. Jun. 2006 vol. 136 No. 6 1558-1564.*
Faure et al. "Specific Amino Acids Increase Mucin Synthesis and Microbiota in Dextran Sulfate Sodium-Treated Rats" The Journal of Nutrition, 2006, vol. 136, pp. 1558-1564.

* cited by examiner

*Primary Examiner* — Jared Barsky
(74) *Attorney, Agent, or Firm* — K&L Gates LLP

(57) ABSTRACT

Compositions and methods are provided that are useful in the treatment of inflammatory bowel disease (IBD) patients. The Compositions and methods are suitable in the prevention or postponement of a relapse in inflammatory bowel disease patients.

14 Claims, No Drawings

NUTRITIONAL COMPOSITION USEFUL IN THE TREATMENT OF IBD PATIENTS

CROSS REFERENCE TO RELATED APPLICATIONS

The present application is a National Stage of International Application No. PCT/EP2016/051275, filed on Jan. 22, 2016, which claims priority to European Patent Application No. 15152309.9, filed on Jan. 23, 2015, the entire contents of which are being incorporated herein by reference.

FIELD OF THE INVENTION

The invention relates to a nutritional composition that is useful in the treatment of inflammatory bowel disease (IBD) patients. Further, the invention relates to a nutritional composition that is suitable in the prevention or postponement of a relapse in inflammatory bowel disease patients.

BACKGROUND OF THE INVENTION

Inflammatory bowel disease (IBD) is a group of inflammatory conditions of the colon and small intestine. The disease may cause severe abdominal pain and nutritional problems (food intolerance and deficiencies). The major types of IBD are Crohn's disease (CD) and ulcerative colitis (UC). CD and UC mainly differ by their location and nature of the inflammatory changes. CD can affect any part of the gastrointestinal tract, from the oral cavity to the anus, with more common clinical manifestations occurring in the ileum and large intestine. UC is restricted to the colon and the rectum.

The etiology of IBD is still not completely understood, but increasing evidence suggests that these disorders occur through an inappropriate immune response to a subset of commensal enteric bacteria in a genetically susceptible host, with disease initiated by environmental triggers. In this regard, sustained intestinal infections, mucosal barrier defects, mucosal immune dysregulation, and genetic and environmental factors all seem to contribute to the disease process.

It is presently unclear how nutritional intake is connected to the disease.

Thus, dietary habits are considered to be a very important environment factor. It is therefore speculated that some nutritional intake may be responsible for inducing, avoiding or potentially treating the disease. Mixtures of prebiotics and probiotics have been used to treat the disease. Beattie et al (1994; Aliment. Pharmacol. Ther.; 8: 1-6) have reported the use of the acid casein fraction in an infant formula in the treatment of 7 children with active small bowel Crohn's disease. U.S. Pat. No. 5,952,295 describes the use of a casein fraction rich in TGF-beta2 for the treatment or prophylaxis of inflammatory conditions of the gastro-intestinal tract, in particular IBD.

Presently, anti-inflammatory drugs, like corticosteroid drugs or mesalazine, antibiotics and, in very severe cases surgery are the preferred choices for treating IBD. While in some cases the above described drugs can already induce clinical remission and reduce intestinal symptoms of IBD, an acute resurgence/relapse of the symptoms can appear following treatment. For example, in children, Crohn's disease has a chronic relapsing course in which up to 50% of the patients eventually need surgery (Davies, G et al; 1990; Br. J. Surg.; 77: 81-94).

The natural clinical course of inflammatory bowel disease (IBD) is characterized by episodes of relapse and remission. The main treatment goal in IBD is to induce and maintain remission by effective control of the gut inflammatory process. Despite the existence of treatments for induction of remission of the disease, the assessment of the level of resolution of the inflammatory process at the intestinal level remains uncertain in the current clinical practice. Subclinical inflammation and incomplete mucosal healing may still persist at the end of a therapeutic cycle that otherwise can be considered successful from a clinical point of view. An "incomplete" biological remission of the inflammatory process is supposed to represent a higher risk for earlier relapse.

In recent years, the gut microbiome has gained increasing attention for its potential role in inflammatory bowel disease (IBD) pathogenesis by triggering abnormal local mucosal inflammatory processes. In fact, *Escherichia coli* has been shown to stimulate the release of proinflammatory cytokines, whereas other bacterial species such as *Lactobacillus casei* and *L. plantarum* downregulate the expression of pro inflammatory cytokines and prevent mucosal damage. Administration of prebiotics, such as oligosaccharides and probiotics (live non-pathogenic bacteria) in animals and healthy human subjects has proven effective for altering the gut microbiome, suggesting that these strategies may be useful in IBD. Despite the general acceptance of the gut microbiota playing a role in IBD etiology and promising preclinical results, probiotic administration has thus far been unsuccessful for maintaining remission or preventing clinical and endoscopic relapse in CD. Disappointing results have also been obtained in randomized controlled trials of prebiotics in CD. In the present application there is provided a nutritional composition that assists in the prevention or postponement of relapse.

SUMMARY

There is now provided a nutritional composition comprising (a) the amino acids threonine, serine, and proline in free form, (b) carbohydrates and proteins comprising whey TGF-Beta, and (c) at least one essential fatty acid.

In an embodiment there is provided a nutritional composition comprising (a) the amino acids threonine, serine, and proline in free form, (b) carbohydrates and proteins comprising whey TGF-Beta, and (c) at least one essential fatty acid for use in the treatment of inflammatory bowel disease (IBD).

In an embodiment there is provided a nutritional composition comprising (a) the amino acids threonine, serine, and proline in free form, (b) carbohydrates and proteins comprising whey TGF-Beta, and (c) at least one essential fatty acid for use in prolonging remission of IBD in an IBD patient.

In an embodiment there is provided a nutritional composition comprising (a) the amino acids threonine, serine, and proline in free form, (b) carbohydrates and proteins comprising whey TGF-Beta, and (c) at least one essential fatty acid for use in maintaining or improving the mucosa health status of an IBD patient.

In an embodiment the composition of the invention may be administered for at least 10, 20, 24, 30, 40, 42, 50, or 60 weeks.

In an embodiment, the administration of a composition accord to the invention is efficacious with respect to the medical indications of claim 2.a, 2.b, or 2.c for at least 10, 20, 24, 30, 40, 42, 50, or 60 weeks or at a time point selected from any time point between 10 and 60 weeks, between 10 and 50 weeks, between 20 and 50 weeks, between 20 and 30 weeks, or between 40 and 50 weeks.

In an embodiment, the IBD is Crohn's Disease (CD) or ulcerative colitis (UC). In a preferred embodiment the IBD is CD.

In an embodiment the composition of the invention may be administered in combination with a medicament effective against IBD, said medicament preferably being an immunosuppressant, preferably a combination of infliximab and adalimumab, or 5-aminosalicylic acid (5-ASA).

In an embodiment the composition according to the invention is in the form of a dry powder formulation.

In an embodiment, the composition according to the invention in the form of a dry powder formulation comprises 9.0-11.0 g threonine in free form, 7.0-9.0 g proline in free form, and 7.0-9.0 g serine in free form, per 100 g of powder formulation.

In an embodiment, the composition according to the invention in the form of a dry powder formulation comprises 20-200 mcg whey TGF-Beta/100 g.

In an embodiment, the composition according to the invention comprises at least one essential fatty acid is selected from the group consisting of alpha-linolenic acid, linolenic acid, eicosapentaenoic acid, and docosahexaenoic acid, or combinations thereof.

In an embodiment, the composition according to the invention in the form of a dry powder formulation comprises 0.1-1.0 g alpha-linolenic acid/100 g, 1.0-8.0 g linolenic acid/100 g, 0.01 g-0.2 g eicosapentaenoic acid/100 g, and 0.005-0.200 g docosahexaenoic acid/100 g.

In an embodiment of the invention the dry powder formulation is reconstituted in water.

In an embodiment the composition of the invention is in the form of a liquid composition. In an embodiment the composition of the invention is in the form of a ready-to-drink, formulation.

In an embodiment, the composition of the invention in the form of a liquid composition, comprises 1.0-3.0 g threonine in free form/100 ml, 1.0-2.5 g serine in free form/100 ml, and 1.0-2.5 g proline in free form/100 ml.

In an embodiment, the composition of the invention in the form of a liquid composition, comprises 10-80 mcg whey TGF-Beta/100 ml.

In an embodiment, the essential fatty acids are selected from the group consisting of alpha-linolenic acid, linolenic acid, eicosapentaenoic acid, and docosahexaenoic acid or combinations thereof.

In another embodiment, there is provided a kit comprising: a first container comprising (a) the amino acids threonine, serine, and proline in free form, and (b) protein and essential fatty acids; and a second container comprising whey TGF-Beta.

In an embodiment there is provided a method of treating IBD, comprising administrating to a patient in need thereof a nutritional composition comprising (a) the amino acids threonine, serine, and proline in free form, (b) carbohydrates and proteins comprising whey TGF-Beta, and (c) at least one essential fatty acid.

In an embodiment there is provided a method of prolonging remission in an IBD patient, comprising administrating to a patient in need thereof a nutritional composition comprising (a) the amino acids threonine, serine, and proline in free form, (b) carbohydrates and proteins comprising whey TGF-Beta, and (c) at least one essential fatty acid.

In an embodiment there is provided a method of maintaining or improving the mucosa health status of an IBD patient, comprising administrating to a patient in need thereof a nutritional composition comprising (a) the amino acids threonine, serine, and proline in free form, (b) carbohydrates and proteins comprising whey TGF-Beta, and (c) at least one essential fatty acid.

DETAILED DESCRIPTION

The invention is directed to a nutritional composition useful for the treatment of IBD or the prevention or postponement of IBD relapse events during remission. All ranges disclosed in this section also cover the integer and/or non-integer values covered by the range.

Inflammatory bowel disease or IBD refers to diseases which cause inflammation in the digestive tract, including Crohn's disease and ulcerative colitis. The causes of IBD are multifactorial and still not completely understood. IBD-associated symptoms include abdominal cramps/pain, bloody diarrhea and weight loss. IBD is characterized by phases of relapse and remission. Treatment of IBD in the sense of the invention comprises prevention or postponement of IBD during remission.

Crohn's disease or CD refers to a chronic inflammatory disorder of the gastrointestinal (GI) tract. It may occur in any portion of the GI tract but is most often found to affect the distal small intestine and/or colon. Unlike ulcerative colitis, CD can affect the entire thickness of the bowel wall. Preferably, the subjects to be treated with the claimed composition are subjects suffering from CD.

Ulcerative colitis or UC refers to a chronic disease marked by inflammation and ulceration of the mucosa (innermost lining) of the colon or large intestine. UC differs from CD in that UC involves only the large intestine, the inflammation involves the entire rectum extending up the colon in a continuous manner without areas of normal intestine interspersed with diseased areas, and UC affects only the innermost lining of the colon.

Enteral feeding means oral or tube feeding.

Milk proteins comprise casein protein and whey protein with the former representing 80% of the milk protein and whey protein 20% of the milk protein. We here refer to cow milk.

Casein is found in milk as a suspension of particles called "casein micelles." The hydrophilic parts reside at the surface and they are spherical. The interior of a casein micelle is highly hydrated. The caseins in the micelles are held together by calcium ions and hydrophobic interactions. Casein proteins comprise alpha-casein, beta-casein, and kappa-casein. Casein proteins are rather insoluble in water.

Casein is prepared from whole milk by microfiltration with the casein (casein micelles) remaining in the retentate while the whey protein can be found in the permeate.

Whey protein comprises a mixture of beta-lactoglobulin (~65%), alpha-lactalbumin (~25%), bovine serum albumin (~8%) and other proteins.

Caseinate is prepared by acid precipitation of casein. Caseinate is more soluble in water than casein (i.e. casein micelles).

A microbiome is the ecological community of commensal, symbiotic, and pathogenic microorganisms that share our body space. "Microbiome" and "microbiota" are defined to describe either the collective genomes of the microorganisms that reside in an environmental niche or the microorganisms themselves, respectively (The NIH HMP Working Group. 2009. The NIH Human Microbiome Project. Genome Res. 2009 December; 19(12): 2317-2323; Backhed, F; Ley, R. E.; Sonnenburg, J. L.; Peterson, D. A.; Gordon, J. I. 2005. Host-Bacterial Mutualism in the Human Intestine. Science 307, 1915 (2005); Turnbaugh, P. J.; Ley, R. E.; Hamady, M.; Fraser-Liggett, C. M.; Knight, R.; Gordon, J. I. 2007. The Human Microbiome Project. Nature. 449:804-810; Ley, R. E.; Peterson, D. A.; Gordon, J. I. 2006. Ecological and Evolutionary Forces Shaping Microbial Diversity in the Human Intestine. Cell. 124: 837-848. DOI 10.1016/j.cell.2006.02.017).

Nutritional Composition

The nutritional composition can be provided as a powder nutritional composition (dry powder formulation), a liquid nutritional composition, or in the form of kit comprising a liquid nutritional composition comprising one or more components of the nutritional composition in one container and comprising in a further container a powder composition, or a second liquid composition, comprising other component(s) of the nutritional composition. The nutritional compositions of the invention are useful for oral consumption or enteral feeding.

In an embodiment, the liquid nutritional composition or the reconstituted powder nutritional composition or liquid nutritional composition derived from the kit can have an energy content of 70-250 kcal/100 ml. In an embodiment, the liquid nutritional composition or the reconstituted powder nutritional composition or liquid nutritional composition derived from the kit can have an energy content of 70-200 kcal/100 ml. In an embodiment, the liquid nutritional composition or the reconstituted powder nutritional composition or liquid nutritional composition derived from the kit can have an energy content of 70-140 kcal/100 ml. In a preferred embodiment, the liquid nutritional composition or the reconstituted powder nutritional composition or liquid nutritional composition derived from the kit can have an energy content of 80-130 kcal/100 ml. In an embodiment, the liquid nutritional composition or the reconstituted powder nutritional composition or liquid nutritional composition derived from the kit can have an energy content of 80-120 kcal/100 ml. In an embodiment, the liquid nutritional composition or the reconstituted powder nutritional composition or liquid nutritional composition derived from the kit can have an energy content of 90-110 kcal/100 ml.

The nutritional composition preferably comprises carbohydrates, protein and fat.

In an embodiment carbohydrates can provide 10-50 energy percent, 20-40 energy percent, or 25-35 energy percent of the composition; total protein (including free amino acids) can provide 30-60 energy percent, 35-55 energy percent, or 40-50 energy percent of the composition; and fat can provide 10-40 energy percent, 15-35 energy percent, or 18-30 energy percent, or 20-25 energy percent of the composition.

In an embodiment carbohydrates can provide 10-50 energy percent of the composition; total protein (including amino acids in free form) can provide 30-60 energy of the composition; and fat can provide 10-40 energy percent of the composition. In an embodiment carbohydrates can provide 20-40 energy percent of the composition; total protein (including amino acids in free form) can provide 35-55 energy of the composition; and fat can provide 15-35 energy percent of the composition. In an embodiment carbohydrates can provide 25-35 energy percent of the composition; total protein (including amino acids in free form) can provide 40-50 energy of the composition; and fat can provide 18-25 energy percent of the composition.

Liquid Nutritional Composition

The liquid enteral nutritional composition according to the invention may have the form of a complete food, i.e. it can meet all nutritional needs of the user. As such, it preferably contains 1200 to 2500 kcal per daily dosage. The daily dosage amounts are given with respect to a daily energy supply of 2000 kcal to a healthy adult having a body weight of 70 kg. For persons of different condition and different body weight, the levels should be adapted accordingly. It is understood that the average daily energy intake preferably is about 2000 kcal. The complete food can be in the form of multiple dosage units. For example to provide an energy supply of 2000 kcal/day using a liquid enteral nutritional composition according to the invention of 2.0 kcal/ml, from 4 (250 ml/unit) to 20 (50 ml/unit) per day may be given.

The liquid enteral nutritional composition can also be a food supplement, for example to be used in addition to a non-medical food. Preferably as a supplement, the liquid enteral nutritional composition contains per daily dosage less than 1500 kcal, in particular as a supplement, the liquid enteral nutritional composition contains 400 to 1000 kcal per daily dose.

The food supplement can be in the form of a single dosage unit per day, or can be in the form of multiple dosage units, e.g. from 2 to 10 dosage units per day. In one embodiment of the present invention, a unit dosage comprises any amount of the liquid enteral nutritional composition according to the invention between 10 ml and 250 ml, the end values of this range included, preferably any amount between 25 ml and 200 ml, the end values of this range included, more preferably any amount between 50 ml and 150 ml, the end values of this range included. In one embodiment of the present invention, a unit dosage comprises about 135 ml. In one embodiment of the present invention, a unit dosage comprises about 125 ml. In one embodiment of the present invention, the composition is provided in a ready to use liquid form and does not require reconstitution or mixing prior to use. The composition according to the invention can be tube fed or administered orally. For example, the composition according to the invention can be provided in a can, in a carton, in a bottle, in a pouch, and/or hang bag.

Powder Nutritional Composition

A composition may be provided to a person in need thereof in powder form, suitable for reconstitution using an aqueous solution or water such that the composition according to the invention is produced. Thus in one embodiment of the present invention, the present composition is in the form of a powder, accompanied with instructions to dissolve or reconstitute in an aqueous composition or water to arrive at the liquid nutritional enteral composition according to the present invention. In one embodiment of the present invention, the present liquid nutritional enteral composition may thus be obtained by dissolving or reconstituting a powder, preferably in an aqueous composition, in particular water.

Viscosity

The powder nutritional composition after reconstitution in water and the ready to use composition preferably have a viscosity of 10-100 mPa·s. at room temperature.

Heat Treatment

The nutritional composition according to the invention is heat-treated in order to make the composition suitable for commercial use, i.e. the nutritional composition according to the invention is subjected to a heat-treatment such as pasteurization or sterilization such that the microbacterial load is reduced.

Packaging

In one embodiment of the present invention, the composition according to the invention, either in powder or liquid form, is packaged. The packaging may have any suitable form of a container, for example a sachet, carton, bottle, pouch, cups, tube, beaker, or capsule. The carton or plastic/glass beaker or tube may have a removable cover; a bottle for example for the 80 ml to 250 ml range, and cups for example for the 10 ml to 30 ml range. Another suitable packaging mode is a powder in a container, e.g. a sachet, preferably with instructions to dissolve or reconstitute in an aqueous composition or water. The containers may be packed into a carton.

Amino Acids

The nutritional composition of the invention comprises the amino acids threonine, serine, and proline both in bound and in free form. We refer to the combined amount of the amino acids in the bound and in the free form as the amount in toto.

In the bound form the amino acids are contained in proteins.

In an embodiment, the liquid nutritional formulation comprises in toto 1.0 g-4 g proline/100 ml. In an embodiment, the liquid nutritional formulation comprises in toto 1.5 g-3.0 g proline/100 ml. In an embodiment, the liquid nutritional formulation comprises in toto or 1.8-2.5 g proline/100 ml.

In an embodiment, the liquid nutritional formulation comprises 0.6 g-3.0 g proline in the free form/100 ml. In an embodiment, the liquid nutritional formulation comprises 1.0 g-2.5 g proline in the free form/100 ml. In an embodiment, the liquid nutritional formulation comprises 1.5-2.0 g proline in the free form/100 ml.

In an embodiment, the liquid nutritional formulation comprises in toto 1.0 g-4 g serine/100 ml. In an embodiment, the liquid nutritional formulation comprises in toto 1.5 g-3.0 g serine/100 ml. In an embodiment, the liquid nutritional formulation comprises in toto, or 1.8-2.5 g serine/100 ml.

In an embodiment, the liquid nutritional formulation comprises 0.6 g-3.0 g serine in the free form/100 ml. In an embodiment, the liquid nutritional formulation comprises 1.0 g-2.5 g serine in the free form/100 ml. In an embodiment, the liquid nutritional formulation comprises 1.5-2.0 g serine in the free form/100 ml.

In an embodiment, the liquid nutritional formulation comprises in toto 1.5-4.0 g threonine/100 ml. In an embodiment, the liquid nutritional formulation comprises 2.0-3.5 g threonine/100 ml. In an embodiment, the liquid nutritional formulation comprises 2.2-3.0 g threonine/100 ml.

In an embodiment, the liquid nutritional formulation comprises 1.0-3.5 g threonine in the free form/100 ml In an embodiment, the liquid nutritional formulation comprises 1.5-3.0 g threonine in the free form/100 ml. In an embodiment, the liquid nutritional formulation comprises 1.8-2.5 g threonine in the free form/100 ml.

In an embodiment, the powder nutritional formulation comprises in toto 5.0-15.0 g proline/100 g. In an embodiment, the powder nutritional formulation comprises 7.0-13.0 g proline/100 g. In an embodiment, the powder nutritional formulation comprises 8.5-11.0 g proline/100 g.

In an embodiment, the powder nutritional formulation comprises 4.0-12.0 g proline in the free form/100 g. In an embodiment, the powder nutritional formulation comprises 6.0-10.0 g proline in the free form/100 g. In an embodiment, the powder nutritional formulation comprises 7.0-9.0 g proline in the free form/100 g. In an embodiment, the powder nutritional formulation comprises 7.3 to 8.5 g proline in the free form/100 g.

In an embodiment, the powder nutritional formulation comprises in toto 5.0-15.0 g serine/100 g. In an embodiment, the powder nutritional formulation comprises 7.0-13.0 g serine/100 g. In an embodiment, the powder nutritional formulation comprises 8.5-11.0 g serine/100 g.

In an embodiment, the powder nutritional formulation comprises 4.0-12.0 g serine in the free form/100 g. In an embodiment, the powder nutritional formulation comprises 6.0-10.0 g serine in the free form/100 g. In an embodiment, the powder nutritional formulation comprises 7.0-9.0 g serine in the free form/100 g. In an embodiment, the powder nutritional formulation comprises 7.5 to 8.7 g serine in the free form/100 g.

In an embodiment, the powder nutritional formulation comprises in toto 7.0-16.0 g threonine/100 g. In an embodiment, the powder nutritional formulation comprises 9.0-14.0 g threonine/100 g. In an embodiment, the powder nutritional formulation comprises or 10.0-13.0 g threonine/100 g. In an embodiment, the powder nutritional formulation comprises 11.0-12.0 g threonine/100 g.

In an embodiment, the powder nutritional formulation comprises 6.0-14.0 g threonine in the free form/100 g. In an embodiment, the powder nutritional formulation comprises 8.0-12.0 g threonine in the free form/100 g. In an embodiment, the powder nutritional formulation comprises 9.0-11.0 g threonine in the free form/100 g. In an embodiment, the powder nutritional formulation comprises 9.4-10.4 g threonine in the free form/100 g.

Protein

The nutritional composition comprises protein or a protein component, in addition to the amino acids proline, serine and threonine in free form, wherein one of the proteins is whey TGF-beta.

The total amount of protein, including amino acids in free form, is referred to as the amount of protein in toto.

In an embodiment, the liquid nutritional composition can comprise in toto 5-20 g protein/100 ml. In an embodiment, the liquid nutritional composition comprises in toto 6-18 g protein/100 ml. In an embodiment, the liquid nutritional composition comprises in toto 6-16 g protein/100 ml. In an embodiment, the liquid nutritional composition comprises in toto 8-16 g protein/100 ml. In an embodiment, the liquid nutritional composition comprises in toto 8-14 g protein/100 ml of protein.

In an embodiment, the powder nutritional composition can comprise in toto 20-80 g protein/100 g. In an embodiment, the powder nutritional composition comprises in toto 30-70 g protein/100 g—In an embodiment, the powder nutritional composition comprises in toto or 40-60 g protein/100 g The protein preferably comprises one or more dairy-protein. In a preferred embodiment the protein can comprise micellar casein, caseinate or whey, or any combination thereof.

In a preferred embodiment, the liquid nutritional composition comprises whey protein.

In a preferred embodiment, the powder nutritional composition comprises caseinate and whey proteins.

Caseinate can be Na-caseinate, Mg-caseinate, K-caseinate, Ca-caseinate or any mixture thereof or combinations thereof such as Na/K-caseinate and Na/Mg caseinate are used as the source of caseinate. Preferably, Ca-caseinate, or a caseinate comprising Ca is not used when micellar casein is used because micellar casein already contains a sufficient amount of calcium, and the formation of further calcium crystals is not desired.

In an embodiment, the liquid nutritional composition can comprise 0.5-5 g of caseinate/100 ml. In an embodiment, the liquid nutritional composition can comprise 1-4 g caseinate/

100 ml. In an embodiment, the liquid nutritional composition can comprise 1.5-3.5 g caseinate/100 ml.

In an embodiment, the powder nutritional composition can comprise 2-10 g caseinate/100 g In an embodiment, the powder nutritional composition can comprise 3-8 g caseinate/100 g. In an embodiment, the powder nutritional composition can comprise 4-6 g caseinate/100 g.

If the nutritional composition comprises casein, in an embodiment the liquid nutritional composition can comprise 0.5-5 g casein/100 ml. In an embodiment the liquid nutritional composition can comprise 1-4 g casein/100 ml. In an embodiment the liquid nutritional composition can comprise 1-3 g casein/100 ml.

If the nutritional composition comprises casein, in an embodiment the powder nutritional composition can comprise 1-8 g casein/100 g. In an embodiment the powder nutritional composition can comprise 2-7 g casein/100 g. In an embodiment the powder nutritional composition can comprise 3-6 g casein/100 g.

Whey protein in the sense of the invention is crude whey protein which is obtained by microfiltration or whey protein isolate which is obtained by further filtration steps removing all components except for the protein. Whey protein isolate differs from whey protein in general in that it does not contain any other molecules than water and protein. Whey protein isolate is virtually or factually lactose free, carbohydrate free, fat free, and cholesterol free while whey protein can still contain lactose, carbohydrates, fat or cholesterol. The nutritional compositions of the invention can thus contain whey protein which is crude whey protein or whey protein isolate, or a combination thereof.

In an embodiment, the liquid nutritional composition can comprise 1-15 g whey protein/100 ml. In an embodiment, the liquid nutritional composition can comprise 2-10 g whey protein/100 ml. In an embodiment, the liquid nutritional composition can comprise 3-8 g whey protein/100 ml. In an embodiment, the liquid nutritional composition can comprise 4-6 g whey protein/100 ml.

In an embodiment, the powder nutritional composition can comprise 5-50 g whey protein/100 g. In an embodiment, the powder nutritional composition can comprise 10-40 g whey protein/100 g. In an embodiment, the powder nutritional composition can comprise 15-30 g whey protein/100 g. In an embodiment, the powder nutritional composition can comprise 20-25 g whey protein/100 g.

If the protein comprises casein and caseinates, the weight ratio of micellar casein to caseinate preferably ranges from 90:10 to 35:65, more preferably from 80:20 to 40:60.

If whey is present, together with caseinate and/or micellar casein, the weight ratio of micellar casein and/or caseinate to whey can range from 95:5 to 70:30.

The osmolarity of the composition can preferably be lower than 900 mOsm/l, preferably lower than 800 mOsm/l, or lower than 700 mOsm/l.

The density of the composition can preferably range between 1.0 g/ml and 1.20 g/ml or between 1.02 g/ml and 1.18 g/ml.

The protein component comprises TGF-beta.

The term TGF-beta designates a family of different growth factors, in particular, TGF-beta 1 and TGF-beta 2 which are two homologous forms of TGF-beta. They are homodimeric and consist of two polypeptide chains each containing 112 amino-acids which are linked by a disulfide bridge. Their molecular mass is 25,000 Daltons. Cow's milk derived whey contains both TGF-beta 1 or TGF-beta 2. TGF-beta 2 is the main component and represents 90% in weight of TGF-beta found in milk, while TGF-beta 1, on the other hand, represents 10% in weight of the total TGF-beta content in milk.

TGF-beta content in milk can be from 12 to 150 µg/l in colostrum, from 3.7 to 3.8 µg/l in crude and pasteurized milk, 4.3 µg/l in skimmed milk, and 3.7 µg/l in whey.

Biological activities of TGF-beta are numerous, which give to this polypeptide a great therapeutical interest for prevention or treatment of a large variety of diseases or pathologies.

TGF-beta is inter alia an anti-inflammatory agent because it decreases pro-inflammatory cytokines production. Thus, it has immunosuppressive properties and inhibits the proliferation of activated T-lymphocytes.

TGF-beta is present in whey protein. It is also possible to provide preparations of whey that contain TGF-beta in higher amounts than crude whey. A process for the preparation of whey TGF-beta which comprises both whey TGF-beta 1 and 2 from whey is described European patent application no. EP 0 527 283 which is herewith incorporated by reference.

However, for the invention the source of whey TGF-beta is not decisive as long as TGF-beta is present in the composition. Preferably, TGF-beta is present in the amounts described in the following:

In an embodiment, the liquid nutritional composition can preferably comprise 10-80 mcg TGF-Beta/100 ml, preferably 20-70 mcg TGF-Beta/100 ml, or 30-60 mcg TGF-beta/100 ml.

In an embodiment, the dry powder formulation can preferably comprise 20-200 mcg TGF-beta/100 g, preferably 30-180 mcg TGF-beta/100 g; or 40-150 mcg TGF-beta/100 g.

The amount of whey TGF-beta can be determined by any standard procedure, in particular, with the means of antibodies against whey TGF-beta in an Enzyme-linked Immunosorbent Assay (ELISA).

Oil and Essential Fatty Acids

The nutritional composition comprises oil and, particularly, essential fatty acids.

In an embodiment, the nutritional composition can comprise essential fatty acids linoleic acid (LA, 18:2n-6), alpha-linolenic acid (ALA, 18:3n-3), docosahexaenoic acid (DHA, 22:6n-3), or eicosapentaenoic acid (EPA, 20:5n-3), or combinations thereof. In a preferred embodiment, all of these essential fatty acids are comprised in the nutritional composition.

In an embodiment, the powder nutritional composition can comprise essential fatty acids in an amount of 0.05-0.4 g/100 g, 0.01-0.5 g, 100 g, or 0.1-0.3 g/100 g.

In an embodiment, the powder nutritional composition can comprise alpha-linolenic acid in an amount of 0.05-1.75 g/100 g, 0.1-1.0 g/100 g, or 0.2-0.5 g/100 g.

In an embodiment, the powder nutritional composition can comprise linolenic acid in an amount of 0.5-9.0 g/100 g, 1.0-8.0 g/100 g, or 1.5-5.0 g/100 g.

In an embodiment, the powder nutritional composition can comprise eicosapentaenoic acid in an amount of 0.010 g/100 g-0.200 g/100 g, 0.025 g/100 g-0.175 g/100 g, or 0.030 g/100 g-0.150 g/100 g.

In an embodiment, the powder nutritional composition can comprise docosahexaenoic acid in an amount of 0.005-0.200 g/100 g, 0.01-0.175 g/100 g, or 0.010-150 g/100 g.

In an embodiment, the liquid nutritional composition can comprise 0.005-1.75 g/100 ml, 0.01-1.25 g/100 ml, 0.02-1.0 g/100 ml alpha-linolenic acid.

In an embodiment, the liquid nutritional composition can comprise linolenic acid in an amount of 0.5-9.0 g/100 ml, 1.0-8.0 g/100 ml, or 1.5-7.5 g/100 ml.

In an embodiment, the liquid nutritional composition can comprise eicosapentaenoic acid in an amount of 0.010 g-0.200 g/100 ml, 0.025 0.175 g/100 ml, or 0.030-0.150 g/100 ml.

In an embodiment, the liquid nutritional composition can comprise docosahexaenoic acid in an amount of 0.005-0.200 g/100 ml, 0.01-0.175 g/100 ml, or 0.010-150 g/100 ml.

In an embodiment, preferably the ratio of the eicosapentaenoic acid to docosahexaenoic acid in the powder and the liquid formulation is from 5:1 to 1:5, 2:1 to 1:2, or 1.2:1 to 1:1.2.

In an embodiment, the oil fraction in the powder and the liquid formulation can comprise at least one medium chain fatty acid (MCFA) or/and at least one mono-unsaturated fatty acid (MUFA).

Carbohydrates

The carbohydrates to be included into the composition can be digestible carbohydrates or indigestible carbohydrates. Digestible carbohydrates are digested to deliver monosaccharides that are then absorbed in the small intestine, while indigestible carbohydrates are not digested and reach the colon.

In an embodiment, the compositions of the invention can comprise digestible carbohydrates or/and indigestible carbohydrates.

The digestible carbohydrates can be sucrose, glucose, glucose syrup, corn starch, or any combination thereof.

The indigestible carbohydrates can be resistant starches, pectins, mucilages, hemicellulose, cellulose, maltodextrin, inulin, oligofructose, and gums.

Additional Components

The nutritional composition can comprise further ingredients like acidulants, flavors, vitamins, minerals, emulsifiers, stabilizers, colorants or gums.

Acidulants to be used in the composition are food grade acidulants and can be citric acid, phosphoric acid, orthophosphoric acid, or any acidulant.

The nutritional composition can comprise at least one vitamin or preferably a vitamin mix. The vitamins are preferably selected from the group consisting of vitamin A, vitamin D3, vitamin E, vitamin C, vitamin B1, vitamin B2, vitamin B6, niacin, folic acid, vitamin B12, choline, panthotenic acid, or biotin or any combination thereof. In a preferred embodiment the composition comprises all vitamins listed above.

Emulgators to be used in the invention are food grade emulgators and can be lecithin, mono and diglycerides of food grade fatty acids, sugar esters of food grade fatty acids.

The nutritional composition can comprise at least one micronutrient, mineral or preferably a mineral or micronutrient mix. The micronutrients are preferably selected from a group consisting of iron, copper, iodine, selenium, manganese, chromium, molybdenum, calcium, magnesium, potassium, sodium, and zinc, or any combination thereof. In a preferred embodiment all of these micronutrients are included into the nutritional composition of the invention. They can be added to the nutritional composition in the form of food grade salts.

Kits

The invention also relates to kits which differ from the liquid nutritional composition of the invention merely in that a liquid or dry composition containing whey TGF-beta is kept in a separate container.

Thus, the invention also relates to a kit comprising a first container comprising a further liquid composition the amino acids threonine, serine, and proline in free form and protein and essential fatty acids. The kit also contains a second container comprising whey TGF-beta. The kit might also contain a third or more further containers containing one or more additional components as described above in relation to the liquid nutritional composition if this is desired.

The first container can thus contain all components and exhibit all characteristics that have been described above in relation to the liquid nutritional composition. The concentrations of the components of the first container will be adapted in a way that after mixing the content of the second container with the content of the first container the final concentrations will have the values that have been described for the liquid nutritional composition.

The second container will contain a composition comprising TGF-Beta in an amount that after mixing the content of the second container to the content of the first container TGF-Beta will be present in an amount that has been described above for the liquid nutritional composition. TGF-Beta can be present in a liquid or dry form.

The composition in the first container might have a volume of 10-500 ml, 20-400 ml, 30-300 ml, 20-200 ml, or 50-100 ml.

The composition in the second container might have a volume of 1-50 ml, 2-40 ml, 3-30 ml, 2-20 ml, or 5-10 ml.

The ratio of the compositions in the first container to the container in the second container can be 10:1, 50:1, or 100:1.

The mixing of the contents of the first container and the second container might occur in the first container. In that case as size of the first container is chosen that allows the addition of the second container without any spill over. Alternatively or in addition, a third container is contained in the kit that has a volume that allows the combination and mixing of the contents of the first and the second container. Mixing the components of the kit will result in a liquid nutritional composition reconstituted from the compositions contained in the two containers.

Medical Uses and Methods

The compositions including those contained in the kits can be used in the treatment of subjects. The compositions are suitable for enterable feeding. Thus, they can be administered orally or via tube feeding.

The invention thus also relates to the nutritional composition of the invention for use in the treatment of IBD, for use in the treatment of a subject being in remission of IBD, or for use in delaying or preventing a relapse of IBD in a subject, or prolonging remission of IBD.

Preferably, the composition of the invention is for use in the treatment of inflammatory bowel disease (IBD), prolonging remission of IBD, or in maintaining or improving the mucosa health status of an IBD patient.

IBD can be Crohn's Disease (CD) or ulcerative colitis (UC), CD is preferred.

In an embodiment the composition of the invention can be administered for at least 10, 20, 24, 30, 40, 42, 50, or 60 weeks. The composition of the invention can preferably be administered for between 10 and 60 weeks, between 20 and 50 weeks, between 15 and 30 weeks, or between 35 and 45 weeks.

The composition of the invention can maintain or improve the mucosa health status of an IBD patient, as indicated by the maintenance of an endoscopic-proven healthy mucosa.

The maintenance of the endoscopic-proven healthy mucosa can be assessed by the simple endoscopic score-Crohn's Disease (SES-CD).

Thus, the improvement of the endoscopic-proven healthy mucosa can be indicated by a reduction in the mean SES-CD score from the onset of administration of the composition of the invention to a time point between 20 and 45 weeks, preferably 20 and 30 weeks, for example week 24, after the onset of administration of the composition of the invention (endoscopic improvement).

The maintenance of the endoscopic-proven healthy mucosa can be indicated by a maintenance of the endoscopic response, wherein an endoscopic response is indicated as effecting an SES-CD decrease of at least 3 points from the onset of administration of the composition of the invention to a time point between 20 and 45 weeks, preferably between 20 and 30 weeks, for example week 24, after the onset of administration of the composition of the invention.

The maintenance of the endoscopic-proven healthy mucosa can also be indicated by a maintenance of the clinical remission, wherein clinical remission is indicated as effecting a CDAI of less than 150 points at a time point of between 20 and 45 weeks, preferably 20 and 30 weeks, for example week 24, after the onset of administration of the composition of the invention.

The composition of the invention can prolong the time until endoscopic or clinical relapse.

The composition of the invention can reduce the economic impact of CD as indicated by surgery, hospitalization and CD complication rates.

The composition of the invention can improve quality of life as indicated, for instance, by IBDQ, SF-36v2 and EQ-5 determined at a time point of between 20 and 45 weeks, preferably 20 and 30 weeks, for example week 24, after the onset of administration of the composition of the invention.

The composition of the invention can improve the composition and functionality of the gut microbiome.

The composition of the invention can improve non-invasive biomarkers like CRP or fecal calprotectin.

The composition of the invention is also characterized in that the administration of said composition is efficacious with respect to the medical indications indicated above for at least 10, 20, 24, 30, 40, 42, 50, or 60 weeks or at a time point selected from any time point between 10 and 60 weeks, between 10 and 50 weeks, between 20 and 50 weeks, between 20 and 30 weeks, or between 40 and 50 weeks after the onset of administration of the composition.

It is also appreciated that the medical uses described herein can also be implemented as corresponding methods of therapeutical treatment.

In particular, the invention also relates to a method comprising administrating the liquid nutritional composition of the invention or the reconstituted powder nutritional composition of the invention, or the liquid nutritional composition reconstituted from the kit of the invention to a subject having IBD.

Combination with Standard Treatments of IBD

The nutritional composition of the invention can be combined with standard treatments common in the treatment of IBD. These standard treatments comprise surgery, antibiotics, immuno-suppressants and anti-inflammatory drugs Immuno-suppressants can be selected from the group consisting of prednisone, TNF or TNFalpha inhibitors (e.g. infliximab, adalimumab), azathioprine (Imuran), methotrexate, and 6-mercaptopurine. A preferred anti-inflammatory drug is mesalamine (USAN) or 5-aminosalicylic acid (5-amino-2-hydroxybenzoic acid, 5-ASA).

Preferably, the composition is administered in combination with at least one TNF inhibitor or TNF inhibitor therapy. Preferably, the at least one TNF inhibitor is a TNF alpha inhibitor. Preferably the at least one TNF alpha inhibitor is infliximab or adalimumab and most preferred the TNF alpha inhibitors are a combination of infliximab and adalimumab.

Preferred is the administration of any of the above cited immuno-suppressants and anti-inflammatory drugs in combination with the nutritional composition of the invention. The combination results in a cooperative effect of the administered compounds.

The invention also relates to the nutritional composition of the invention for use in the treatment of IBD, for use in the treatment of a subject being in remission of IBD, or for use in preventing or delaying a relapse of IBD in a subject wherein the nutritional compositions is to be administered in combination with medicament effective against IBD, said medicament preferably being an immunosuppressant or 5-aminosalicylic acid (5-ASA). This subject could be a subject that has undergone surgery or will undergo surgery.

The administration of the nutritional composition can occur before, during or after the administration of the above cited drugs.

The invention also relates to a method comprising administrating the liquid nutritional composition of the invention or the reconstituted powder nutritional composition of the invention, or the liquid nutritional composition reconstituted from the kit of the invention and a medicament effective against IBD, said medicament preferably being an immunosuppressant or 5-aminosalicylic acid (5-ASA) to a subject having IBD or a relapse of IBD thereby treating a subject suffering from IBD or to a subject being in remission of IBD and thereby delaying or preventing a relapse of IBD.

The invention also relates to a method comprising administrating the liquid nutritional composition of the invention or the reconstituted powder nutritional composition of the invention, or the liquid nutritional composition reconstituted from the kit of the invention to a subject before undergoing surgery or after having undergone surgery with the aim of treating IBD and thereby treating IBD.

EXAMPLES

Example 1: Powder Nutritional Composition

The following composition is an exemplary powder nutritional composition.

| Component | Percentage |
|---|---|
| Lecithin | 0.6 |
| Micronutrients | 0.15 |
| Maltodextrin | 24.0 |
| Potassium Hydroxide | 0.3 |
| Caseinate Potassium | 6.0 |
| Sucrose | 6.0 |
| Vitamins | 0.5 |
| Protein Whey Isolate enriched for TGF-beta | 1.0 |
| AA Proline | 7.4 |
| AA Serine | 7.4 |
| AA Threonine | 8.8 |
| Whey protein | 27.85 |
| Oil comprising essential fatty acids | 10.0 |
| Total | 100.0 |

30 g of said composition can be reconstituted with about 115 ml of water to yield a composition of about 135 ml.

Example 2: Liquid Nutritional Composition

The following composition is an exemplary liquid nutritional composition.

| Component | g/100 ml |
|---|---|
| Glucose syrup DE 26-32 | 5.5 |
| Sucrose | 3.0 |
| Whey protein | 7.0 |
| Caseinate Na | 3 |
| Vitamins | 0.1 |
| Micronutrients | 0.4 |
| Starch | 0.1 |
| Carrageenan | 0.05 |
| Color Carotene | 0.02 |
| AA Serine | 2.0 |
| AA threonine | 2.5 |
| AA Proline | 2.0 |
| Protein Whey Isolate comprising TGF-Beta | 0.4 |
| Oil comprising essential fatty acids | 3.0 |
| Emulgator | 0.3 |

Example 3: Clinical Trial

A clinical trial is performed. This is a double-blinded study to evaluate the efficacy of Crown Nx in maintaining remission in CD.

Number and Selection of Subjects:

Approximately 250 subjects with mild to moderately active CD will be screened to identify 216 eligible subjects to be randomized.

Included are adults (18-75 years) with a known history of symptomatic CD confirmed by endoscopy or radiology, clinical remission or mild- to moderate disease (CDAI score 0-300 inclusive), active endoscopic disease (SES-CD score≥4) documented during the study screening phase, able to consume oral nutrition for up to 24 weeks and optionally initiation of induction infliximab or adalimumab therapy at least 12 weeks prior to randomization (maximum 20 weeks).

Composition to be Tested and Regimen

The composition is a nutritionally-based, anti-inflammatory therapy with a high protein content consisting of whey and casein protein (14 g per serving), whey-TGFβ (10-40 mcg TGF-beta per serving), plus the free amino acids: threonine in free form (3.3 g per serving), serine in free form (2.75 g per serving) and proline in free form (2.75 g per serving).

The placebo is an appearance and volume-matched formulation consisting of maltodextrin and skimmed milk powder, which will be used in the control group.

The composition is provided in a powder formulation that is reconstituted with 120 ml of water, which yield to a 135 mL formulation. Patients take 2 times 135 ml servings orally between meals each day for 24 weeks.

Assessment of Efficacy

The study is a randomized placebo-controlled trial to assess the impact of a nutritional intervention in the maintenance and improvement of the intestinal mucosa health status of CD's patients. The shift in the patient's nutritional status is hypothesized to be achieved through the administration of the medical food.

The assessment of the effectiveness of the composition is based on the results of colonoscopy, biopsy, questionnaires and other parameters as explained below.

Colonoscopy is performed during the study screening phase and at week 24 after initiating the treatment with the medical food. Colonoscopy includes SES-CD scoring.

At each colonoscopy, biopsies are taken and assessed for the presence of inflammation, e.g. using the global histologic disease activity score.

In addition questionnaires are to be completed by the participants of the study (for instance, SF-36v2, EQ-5D, WPAI-CD) and other parameters determined (fecal calprotectin, c-reactive protein, fecal microbiome). The nutritional status of patients are recorded (weight gain, albumin & pre-albumin levels, serum levels of AAs amd micronutrients, BMI, % body fat)

A significant improvement or maintenance of the values of the parameters compared to the values determined in the control group is indicative for the effectiveness of the administration of the composition.

Assessed Parameters

SES-CD

The simple endoscopic score for Crohn's Disease (SES-CD, Mary J Y, Modigliani R. Development and validation of an endoscopic index of the severity for Crohn's disease: a prospective multicentre study. Groupe d'Etudes Therapeutiques des Affections Inflammatoires du Tube Digestif (GETAID). Gut 1989; 30:983-9; Daperno M, D'Haens G, Van Assche G, et al. Development and validation of a new, simplified endoscopic activity score for Crohn's disease: the SES-CD. Gastrointest Endosc 2004; 60:505-12.) evaluates 4 endoscopic variables (ulcer size, proportion of the surface area that is ulcerated, proportion of the surface area affected, and stenosis) by scoring each variable on a scale from 0 to 3 where higher scores indicate more severe disease, in five colonic segments (ileum, right colon, transverse colon, left colon, and rectum).

| Definitions of SES-CD | | | | |
|---|---|---|---|---|
| | SES-CD values | | | |
| Variable | 0 | 1 | 2 | 3 |
| Ulcers | None | Aphthous ulcers (Diameter 0.1-0.5 cm) | Large ulcers (Diameter 0.5-2 cm) | Very large ulcers (Diameter >2 cm) |
| Ulcerated surface | None | <10% | 10-30% | >30% |
| Affected surface | Unaffected segment | <50% | 70-75% | >75% |
| Stenosis | None | Single, can be passed | Multiple, can be passed | Cannot be passed |

The score for each endoscopic variable is the sum of the values obtained for each segment. The SES-CD Total is the sum of the 4 endoscopic variable scores.

Definitions of Endoscopic Response and Remission are Based Upon the SES-CD as Follows:

Endoscopic Improvement: Reduction in the mean SES-CD score from baseline to Week 24.

Endoscopic Response: SES-CD decrease of at least 3 points

Endoscopic Remission: SES-CD less than 4 points

Crohn's Disease Activity Index (CDAI)

The Crohn's disease activity index (CDAI) score provides a measurement of the active status of Crohn's disease in a patient over a given week. The CDAI will be calculated combining subject, Investigator and laboratory entries.

Components of the CDAI are the following:

| Variable | Weighting Factor |
|---|---|
| 1. Number of liquid or soft stools each day for seven days | ×2 |
| 2. Abdominal pain (0 = none; 1 = mild; 2 = moderate; 3 = severe) each day for seven days | ×5 |
| 3. General well-being (0 = generally well; 1 = slightly | ×7 |

| Variable | Weighting Factor |
|---|---|
| below par; 2 = poor; 3 = very poor; 4 = terrible) each day for seven days | |
| 4. Presence of complications on day of exam (Add 1 for each category corresponding to subject's symptoms) (a) arthritis/arthralgia (b) skin or mouth lesions (erythema nodosum, pyoderma gangrenosum, or aphthous stomatitis) (c) iritis or uveitis (d) anorectal lesions (fissure, fistula, or abscess) (e) other fistula (f) fever over 37.8 degrees Celsius or 100.04 degrees Fahrenheit | ×20 |
| 5. Use of Lomotil or opiates for diarrhea (yes or no) | ×30 |
| 6. Presence of an abdominal mass (0 = none; 2 = questionable; 5 = definite) | ×10 |
| 7. Hematocrit of <47 in men and <42 in women | ×6 |
| 8. Percentage deviation from standard weight = ([Standard weight − Actual weight]/ Standard weight) × 100 | ×1 |
| CDAI Total | Sum of #1-8 above |

Definitions of Clinical Response and Remission are Based Upon the CDAI as Follows:

Clinical Remission: Crohn's Disease Activity Index (CDAI) less than 150 points

Clinical Response: CDAI decreased by at least 100 points from the randomization visit Global Histologic Disease Activity Score The Global Histologic Disease Activity Score (GHAS) assesses the extent and severity of histologic inflammation in colonic or ileal biopsy samples in CD. 7 characteristic factors are taken into account including epithelial and architecture changes, inflammatory cell infiltrates, erosions or ulcers, granulomas, and an adjustment for the number of biopsy samples affected (D'Haens G R, Geboes K, Peeters M, et al. Early lesions of recurrent Crohn's disease caused by infusion of intestinal contents in excluded ileum. Gastroenterology 1998; 114:262-7; Geboes K, Dalle I. Influence of treatment on morphological features of mucosal inflammation. Gut 2002; 50:iii37-iii42.).

| Histological Variable | Grading |
|---|---|
| 1. Epithelial damage | 0 = normal; 1 = focal; 2 = extensive |
| 2: Architectural changes | 0 = normal; 1 = moderate (>50%); 2 = severe (>50%) |
| 3: Mononuclear cells in lamina propria | 0 = normal; 1 = moderate increase; 2 = severe increase |
| 4: Polymorphonuclear cells in lamina propria | 0 = normal; 1 = moderate increase; 2 = severe increase |
| 5: Neutrophils in epithelium | 1 = surface epithelium; 2 = cryptitis; 3 = crypt abscess |
| 6: Erosion or ulceration | 0 = no; 1 = yes |
| 7: Granuloma | 0 = no; 1 = yes |
| 8: Number of biopsies affected (total: n = 6 or more) | 0 = none; 1 = >33%; 2 = 33-66%; 3 = >66% |
| Total GHAS | The total score is the sum of all individual scores (max = 16) |

Histopathologic Remission: GHAS total≤4
Histopathologic Improvement: GHAS decrease.
SF-36v2

The SF-36 questionnaire (Version 2; SF-36v2;) is a validated generic health-related quality of life instrument which consists of 36 questions aggregated into 8 domains (Smith J J, Netuveli G, Sleight S P, et al. Development of a social morbidity score in patients with chronic ulcerative colitis as a potential guide to treatment. Colorectal Dis 2012; 14:e250-7). These domains are further summarised into two components, a physical component summary (PCS) scale and a mental component summary (MCS) scale. Each scale ranges from 0 to 100 with higher scores indicating better functional status. The SF-36 questionnaire will be self-administered by the study subjects.

EQ-5D

The EQ-5D was developed as a cardinal index of health, which takes into account physical, mental and social functions, and is simple to complete (Stark R G, Reitmeir P, Leidl R, et al. Validity, reliability, and responsiveness of the EQ-5D in inflammatory bowel disease in Germany. Inflamm Bowel Dis 2010; 16:42-51). The questionnaire contains 5 questions: mobility, self-care, usual activities, pain/discomfort and anxiety/depression. The 5 questions are summarized into one global score, the EQ-5D single index. Higher scores are associated with more impairment. In addition, the instrument generates a single numeric index of health status which ranges from 0 to 100 measured on a visual analogue scale, with 0 and 100 indicating worst and best imaginable health state respectively. The EQ-5D questionnaire will be self-administered by the study subjects.

WPAI-CD

The WPAI-CD (Reilly M C, Gerlier L, Brabant Y, et al. Validity, reliability, and responsiveness of the work productivity and activity impairment questionnaire in Crohn's disease. Clin Ther 2008; 30:393-404; Feagan B G, Reilly M C, Gerlier L, et al. Clinical trial: the effects of certolizumab pegol therapy on work productivity in patients with moderate-to-severe Crohn's disease in the PRECiSE 2 study. Aliment Pharmacol Ther 2010; 31:1276-85) consists of 6 questions that evaluate absenteeism (work time missed), presenteeism (reduced work productivity), overall work impairment, and activity impairment. The WPAI-CD questionnaire will be self-administered by the study subjects.

Fecal Calprotectin

Stool samples will be obtained at day 0, at week 12 and at week 24 for the measurement of fecal calprotectin levels.

C-Reactive Protein

C-reactive protein will be assessed at day 0, at week 12 and at week 24. C-reactive protein belongs to the pentraxin family of proteins, is made exclusively in the liver and is secreted in increased amounts within 6 hours of an acute inflammatory stimulus. The plasma level can double at least every 8 hours, reaching a peak after about 50 hours. After effective treatment or removal of the inflammatory stimulus, levels can fall almost as rapidly as the 5-7-hour plasma half-life of labelled exogenous CRP. The only condition that interferes with the "normal" CRP response is severe hepatocellular impairment.

CD is one of the most common conditions associated with major elevations of CRP levels (Vermeire S, Van Assche G, Rutgeerts P. C-reactive protein as a marker for inflammatory bowel disease. Inflamm Bowel Dis 2004; 10:661-5). While an elevated CRP value is not specific for any condition, it is a sensitive index of ongoing inflammation, and thus provides a valuable adjunct to a careful clinical assessment.

Once a diagnosis has been established, CRP may be used to monitor the subject's response to therapy. Serial CRP measurements are important adjuncts in clinical practice, as CRP levels are not affected by drug therapy or thermoregulatory factors. In CD, CRP levels correspond well to disease activity and treatment efficacy (Vermeire S, Van Assche G, Rutgeerts P. C-reactive protein as a marker for inflammatory bowel disease. Inflamm Bowel Dis 2004; 10:661-5).

The invention claimed is:

1. A method for achieving a result selected from the group consisting of treatment of inflammatory bowel disease (IBD), prolonging remission of IBD, and maintaining or improving the mucosa health status of a patient having IBD or in remission from IBD, the method comprising:

administering a composition comprising (a) free form amino acids comprising 9.0-11.0 g threonine in free form/100 g of the composition, 7.0-10.0 g serine in free form/100 g of the composition, and 7.0-9.0 g proline in free form/100 g of the composition; (b) carbohydrates and proteins comprising whey TGF-Beta; and (c) at least one essential fatty acid to the patient, the carbohydrates are 10-50 energy percent of the composition, total proteins comprising the free form amino acids and the proteins comprising the whey TGF-Beta are 30-60 energy percent of the composition, and fats comprising the at least one essential fatty acid are 10-40 energy percent of the composition, the patient has initiated therapy comprising at least one of infliximab or adalimumab at least 12 weeks prior to initiating the administering of the composition to the patient.

2. The method of claim 1, wherein the composition is administered to the patient for at least 10 weeks.

3. The method of claim 1, wherein the administration of the composition is efficacious with respect to medical indications from IBD for a time point selected from any time point between 10 and 60 weeks.

4. The method of claim 1, wherein the IBD is selected from the group consisting of Crohn's Disease and ulcerative colitis.

5. The method of claim 1, wherein the composition is administered in combination with a medicament effective against IBD.

6. The method of claim 1 comprising reconstituting the composition from a dry powder formulation into water.

7. The method of claim 1, wherein the composition comprises 0.1-1.0 g alpha-linolenic acid/100 g, 1.0-8.0 g linolenic acid/100 g, 0.01 g-0.2 g eicosapentaenoic acid/100 g, and 0.005-0.200 g docosahexaenoic acid/100 g.

8. The method of claim 5, wherein the medicament comprises 5-aminosalicylic acid (5-ASA).

9. The method of claim 1, wherein the composition is orally administered to the patient between meals for at least 24 weeks in an amount that contains 400 to 1000 kcal per daily dose.

10. The method of claim 1, wherein the proteins of the composition consist of whey, casein, the threonine in free form, the serine in free form, the proline in free form, and the whey TGF-Beta.

11. The method of claim 1, wherein the threonine in free form, the serine in free form, and the proline in free form are the only free form amino acids in the composition.

12. The method of claim 1, wherein the carbohydrates are 20-40 energy percent of the composition, the total proteins are 35-55 energy percent of the composition, and the fats are 15-35 energy percent of the composition.

13. The method of claim 1, wherein the carbohydrates are 25-35 energy percent of the composition, the total proteins are 40-50 energy percent of the composition, and the fats are 18-25 energy percent of the composition.

14. The method of claim 1, wherein the patient is in remission from IBD.

* * * * *